United States Patent [19]

Quinlan

[11] Patent Number: 4,578,268

[45] Date of Patent: * Mar. 25, 1986

[54] DIETHYLCARBAMAZINE RESINATE AND STYRYLPYRIDINIUM RESINATE-DIETHYLCARBAMAZINE RESINATE EDIBLE ANTHELMINTIC TABLETS FOR COMPANION ANIMALS

[75] Inventor: James M. Quinlan, Trenton, N.J.

[73] Assignee: American Cyanamid Company, Stamford, Conn.

[*] Notice: The portion of the term of this patent subsequent to Apr. 10, 2001 has been disclaimed.

[21] Appl. No.: 580,577

[22] Filed: Feb. 16, 1984

Related U.S. Application Data

[63] Continuation-in-part of Ser. No. 239,966, Mar. 3, 1983, Pat. No. 4,442,086, which is a continuation-in-part of Ser. No. 60,931, Jul. 26, 1979, abandoned.

[51] Int. Cl.$^4$ ............................................. A61K 31/74
[52] U.S. Cl. ............................................................ 424/79
[58] Field of Search ........................................... 424/79

[56] References Cited

U.S. PATENT DOCUMENTS

| | | | |
|---|---|---|---|
| 3,177,116 | 4/1965 | Wood et al. | 424/263 |
| 3,179,559 | 4/1965 | Wood et al. | 424/263 |
| 3,250,623 | 5/1966 | Clair et al. | 424/79 |
| 3,862,312 | 1/1975 | Rimington et al. | 424/79 |

Primary Examiner—Frederick E. Waddell
Attorney, Agent, or Firm—Estelle J. Tsevdos

[57] ABSTRACT

There are provided palatable anthelmintic resinate compositions for companion animals, containing anthelmintically effective amounts of a styrylpyridinium compound and/or an N,N-dialkylpiperazine carboxamide.

9 Claims, No Drawings

DIETHYLCARBAMAZINE RESINATE AND STYRYLPYRIDINIUM RESINATE-DIETHYLCARBAMAZINE RESINATE EDIBLE ANTHELMINTIC TABLETS FOR COMPANION ANIMALS

This application is a continuation-in-part of Ser. No. 239,966 filed Mar. 3, 1983, now U.S. Pat. No. 4,442,086, which is a continuation-in-part of Ser. No. 060,931, filed July 26, 1979, now abandoned.

SUMMARY OF THE INVENTION

The present invention relates to palatable acidic resinate compositions which contain a styrylpyridinium compound and/or an N,N-dialkylpiperazine carboxamide and find utility as palatable anthelmintic compositions for the treatment of helminthiasis in companion animals.

Styrylpyridinium compounds and methods for their preparation are disclosed in U.S. Pat. Nos. 3,177,116 and 3,179,559, issued Apr. 6, 1965 and Apr. 20, 1965, respectively. These patents are incorporated herein by reference. Similarly, N,N-dialkylpiperazine carboxamides are disclosed in U.S. Pat. No. 2,467,895, issued Apr. 19, 1949. This patent is incorporated herein by reference. The above-identified compounds are known to be useful for combatting helminthiasis in domestic animals. They are said to be effective when administered by the oral route. Administration of both the N,N-dialkylpiperazine carboxamides and the styrylpiridinium halides, in the form of capsules, tablets and in the feed, is contemplated by the patentees. However, it has been found that the styrylpyridinium compounds are unpalatable when taken orally and the N,N-dialkylpiperazine carboxamides are only partially acceptable to companion animals when administered in a form in which the active compound is permitted to come in contact with the animals taste buds. Over the years, veterinarians have continually complained that the available tablets, pills or formulated compositions marketed for admixture of the styrylpyridinium halides with feeds is unsatisfactory and has resulted in the reluctance of the animals to ingest the medicated feed, tablets or pills. It would therefore be highly advantageous and most desirable if the above-named compounds could be rendered palatable without destroying their efficacy. Furthermore, it would be most advantageous if a palatable composition, containing a N,N-dialkylpiperazine carboxamide, alone or in combination with a styrylpyridinium compound such as a 1-methyl-2-(p-chlorostyryl)pyridinium salt, could be prepared in the form of a chewable tablet, pill, granulated product or the like.

Heretofore, it has been stated that, "both olfaction and taste are involved in canine food preferences". Thus, the use of split plate evaluations for preference are crucial in delineating olfactory medicated preferences. Actual consumption of an article is a function of combined odor and taste acceptability which is herein interpreted as palatability.

It is, therefore, an object of this invention to provide palatable, therapeutically effective compositions, containing a N,N-dialkylpiperazine carboxamide alone or in combination with a styrylpyridinium compound, useful for the treatment of helminthiasis in companion animals.

It is also an object of the present invention to provide methods for preparing diethylcarbamazine and/or styrylpyridinium compositions which are palatable and stable when admixed with animal feed stuffs.

The present invention accomplishes these objectives by the provision of novel resinates of N,N-dialkylpiperazine carboxamide compounds having the formula:

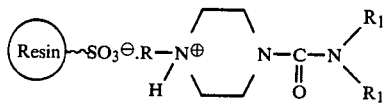

where R is hydrogen or $C_1$–$C_6$ alkyl and $R_1$ is alkyl $C_1$–$C_5$; and of styrylpyridinium compounds having the formula:

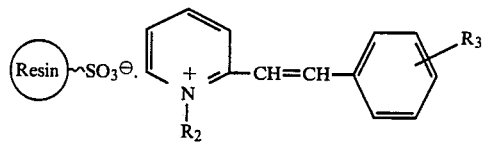

wherein $R_2$ is $C_1$–$C_4$ alkyl and $R_3$ is hydrogen or halogen.

The above compounds are described in U.S. Pat. Nos. 2,467,895 issued Apr. 19, 1949 and 3,177,116 issued Apr. 6, 1965; however, no mention is made by the patentees of resinate forms of said compounds or the improved palatability obtained with said forms.

Palatable anthelmintic resinate compositions are described in copending application for U.S. Letters Patent of James Michael Quinlan, Ser. No. 239,966, filed Mar. 3, 1981, incorporated herein by reference thereto, which discloses the essential matrix for palatability of the subject edible anthelmintic tablets as a composition comprising 1-methyl-2-(p-chlorostyryl)pyridinium resinate and/or resinated diethylcarbamazine, 18% to 60% by weight, and 0% to 40% Brewers yeast.

Since it is sometimes desirable to have tablets of varying sizes, it is the purpose of the present invention to provide palatable edible anthelmintic compositions of a smaller tablet size.

Thus palatable tablets of anthelmintic compositions containing 1-methyl-2-(p-chlostyryl)pyridinium resinate and/or resinated diethylcarbamazine as described in the above-identified application for U.S. Letters Patent of varying sizes and essentially the same potencies may be obtained by maintaining the matrix required for palatability of about 18% to 60% by weight of desiccated liver and 0% to 40% by weight of Brewers yeast in conjunction with the use of said resinated compounds.

The resinates of the above-identified compounds are prepared by reacting the free base or pharmacologically acceptable salt of the N,N-dialkylpiperazine carboxamide or the pharmacologically acceptable salt of the styrylpyridinium compound with an acidic cationic exchange resin under conditions whereby said compound becomes ionically bound to the acidic anion of the resin.

The diethylcarbamazine and/or the styrylpyridinium compound is bonded to the resin with sufficient ionic strength to withstand ionization in the mouths of animals. However, the efficacy of these anthelmintic agents is retained since the active compound is released from the resin in the stomach and/or intestinal tract of the animal after being swallowed.

When the compositions of the present invention are prepared using only the N,N-dialkylpiperazine carboxamide as the anthelmintic agent, the essential ingredients of the compositions are, greater than 5% to about 11% by weight of the N,N-dialkylpiperazine carboxamide resinate, preferably a high capacity sulfonic cationic exchange resin of the polystyrene-divinylbenzene type; 18% to 60% by weight of the desiccated liver; and 0% to 40% of Brewer's yeast.

When two anthelmintic agents are employed in the compositions of the invention, the essential ingredients are; greater than 5% (5.1%) to about 11% by weight of the resinated N,N-dialkylpiperazine carboxamide; greater than 7% (7.1%) to 16% by weight of the styrylpidinium resinate; 18% to 60% by weight of the desiccated liver; and 0% to 40% of Brewer's yeast.

Diluents such as pharmaceutically acceptable binding agents, lubricants and the like, which are in the manufacture of the compositions of the invention are, hereinafter described.

Preparation of the diethylcarbamazine resinate and styrylpyridinium resinate can be achieved by admixing the diethylcarbamazine compound with deionized water or the styrylpyridinium compound with an alcohol deionized water mixture and intimately contacting the resulting mixture with a high capacity, sulfonic acid cationic exchange resin having a 4% to 8% divinylbenzene cross-linkage and a screen size of about 16 to 50 mesh. The thus prepared resinate is then separated from the supernatant liquid and washed repeatedly with deionized water until the wash water has a pH of about 4.5. The resin is then dried and ground or milled to at least about $800\mu$ and preferably to an average particle size between $45\mu$ and $300\mu$. The resinates, thus prepared, can be used separately to formulate edible tablets or they may be admixed to prepare edible tablets containing both compounds.

In the preparation of the above-mentioned resinates, alcohols such as methanol, ethanol, propanol, isopropanol, butanol, isobutanol, pentanol-1, or pentanol-2, may be employed.

Strongly acidic resins are preferred in the preparation of the resinates of this invention since they provide resinates in which the diethylcarbamazine and/or styrylpyridinium compounds are more strongly bonded to the ion exchange resin to substantially prevent the compounds ionizing in the mouth of the animal to which they are fed. Among the preferred strongly acidic resins are sulfonated polystyrenes prepared from styrene and divinylbenzene which functions as a cross-linking agent. These resins include AMBERLITE ®IR-120, and DOWEX ®50 and 50W. Sulfonated phenolic resins, may also be used and may include AMBERLITE ®IR-1; cellulose alkylsulfonic acid resins such as CELLEX SE resin and the like may also be utilized in the preparation of the resinates of this invention.

The reaction to form the resinates can be carried out over a wide temperature range so long as the solvent remains fluid and is not evaporated in excessive amounts. For example, the reactions may be conducted at a temperature between about 0° and 100° C. and preferably at from about 20° to 50° C.

The diethylcarbamazine or styrylpyridinium solution can be contacted with the resin in any convenient manner such as by mixing the solution with the finely divided resin or by passing the solution of the anthelmintic agent through a resin bed. The molar ratio of anthelmintic agent to resin employed is not critical and is usually within the range of 0.125:1 to 3:1, preferably 0.5:1 to 2:1. A ratio within the preferred range permits efficient loading of the resin within a reasonable period of time. The anthelmintic resinates obtained in accordance with this invention contain about 10% to 60% by weight of anthelmintic and preferably about 40% to 55% of said anthelmintic. The resinate compositions can be prepared by either a batch or a continuous process and if desired both the diethylcarbamazine and styrylpyridinium compound may be loaded on a single resin. However, it is essential that in this arrangement the styrylpyridinium be loaded first and then the loaded resin thoroughly washed before the diethylcarbamazine is loaded on the resin. In this practice the resin is loaded only to about 25% to 33% by weight with the styrylpyridinium, determined on the basis of the dry weight on the resin, and then with about 13% to 18% by weight with diethylcarbamazine, determined on the basis of the dry weight of the resin. The preferred loading ration of styrylpyridinium to diethylcarbamazine or sequentially loaded resins is about 1.7 to 1. However, ratios as low as 1.3 to 1 can be used.

The sequentially loaded resinate, containing both the N,N-dialkylpiperazine carboxamide and the styrylpyridinium compound, may be illustrated as follows:

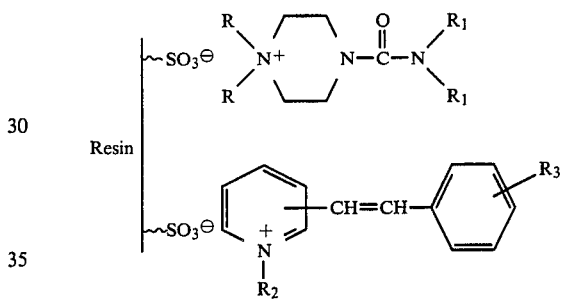

wherein R, $R_1$, $R_2$ and $R_3$ are as described above.

Other embodiments and advantages of this invention will become more apparent from the examples set forth below. These examples are provided for the purpose of demonstrating the invention and are not intended to limit the scope hereof.

EXAMPLE 1

Diethylcarbamazine Resinate

Diethylcarbamazine (1125 kg real, 5.653 kg mole) also named N,N-diethyl-4-methyl-1-piperazinecarboxamide, is charged to 2240 liters of deonized water and agitated to dissolve it. To this solution is then added a high capacity sulfonic cation exchange resin of the polystyrene divinylbenzene type (2380 kg) AMBERLITE IR-120 ® manufactured by Rohm & Haas Co. The reaction slurry is filtered, washed with deionized water (2240 liters), and dried at 80°-90° C. The dried diethylcarbamazine resinate (2380 kg) which assays 45.0% diethylcarbamazine free base is then milled to $-30$ mesh particle size.

The above-mentioned cation exchange resin has a density of 0.85 g/cc apparent, 1.26 g/cc true; water content 44-48%; exchange capacity of 4.40 milliequivalents/g dry and a screen size of from 16 to 50 mesh.

Styrylpyridinium Resinate

A 3960 gram quantity of a sulfonic acid divinylbenzene resin (H+form) calculated to contain 1500 grams or 7.620 equivalents capacity of dry resin is mixed with a solution containing 2074 grams of 1-methyl-2-(p-chlorostyryl)-pyridinium chloride, 3000 ml of methanol and 3900 ml of deionized water. The mixture is diluted to 11,000 ml with deionized water and then allowed to settle and the supernatant liquid separated from the mixture by filtration. This washing treatment is repeated 10 times. The pH of the final wash is 4.50 and the pH of the deionized water is 4.85. The resinate is then dried at 75° C. for 48 hours and weighs 2,739 grams. The resinate passes through a 20 mesh screen and assays 52.38% 1-methyl-2-(p-chlorostyryl)-pyridinium as the chloride and has a KF moisture content of 1.305%. The resin used in the above preparation is marketed under the tradename Powdex by the Graver Water Conditioning Co., N.Y., N.Y. and is essentially 20–50 mesh material.

EXAMPLE 2

Preparation of Diethylcarbamazine Resinate

A mixture of 20–50 mesh washed Powdex resin (1667 g wet resin, calculated to contain 698.0 g dry resin or 3.546 equivalents capacity) and 500 ml of deionized water are mixed in a vessel. To this mixture is added 719.28 g (706.6 g, real; 3.546 moles) of diethylcarbamazine base. The mixture is stirred for 4 hours and then filtered and washed repeatedly with deionized water. The resinate is collected and dried at 85° C. for 24 hours. The dried resinate weighs 1389 g and assays 50.59% and 50.30% diethylcarbamazine base.

EXAMPLE 3

Preparation of diethylcarbamazine resinate-styrylpyridinium resinate edible tablets Diethylcarbamazine resinate (6924 kg 9.89% w/w) and 1-methyl-2-(p-chlorostyryl)-pyridinium resinate (106.25 kg 15.18% w/w) prepared in accordance with Example 1 are blended with 0.35 kg of colloidal silicon dioxide. Desiccated-granular liver (140.0 kg 20.0% w/w) is screened through a 30 mesh screen and admixed with the resinate mixture. Brewer's yeast (125.15 kg 17.88 w/w) is then passed through a 30 mesh screen and mixed with the previously prepared resinate mixture. Microcrystalline cellulose (210.00 kg) and 49.00 kg of stearic acid are blended with the above-noted mixture and the resulting formulation formed into 0.70 g tablets using a commercial tableting machine.

EXAMPLE 4

Palatability evaluation of diethylcarbamazine edible tablets

The following test was conducted to determine what effect 0% to 7% stearic acid has on the palatability of the chewable tablets of the present invention.

Nine sexually mature beagle dogs were demonstrated to be heartworm (*Dirofilaria immitis*) free and housed such that each dog could be tested individually. Three two-day phases of testing were performed. At least one day with no presentations was allowed between phases. On each of the two successive test days, two presentations (a.m. and p.m.) of two tablet formulations were made to each dog. The tablets were positioned about six inches apart on the floor with their relative positions reversed at each successive presentation. Approximately two minutes were allowed for the dogs to voluntarily accept (eat) or reject the tablet(s). Records were maintained for each tablet formulation, presentation, and dog to reflect tablet acceptance or rejection. The percentage of the total number of tablet presentations which were accepted were calculated for each formulation.

The tablets used in these evaluations had the following compositions:

1. Conventional diethylcarbamazine tablets containing *non-resinated* diethylcarbamazine citrate 50 mg per tablet.
2. Diethylcarbamazine resinate plus binder.

These tablets are prepared by blending diethylcarbamazine resinate (16.4 g 3.28% W/W), prepared as described in Example 1 above, with microcrystalline cellulose (483.6 g 96.8% W/W). The blended mixture is slugged, milled and compacted on a commercial tableting maching to give ¾-inch round tablets weighing 1.95 g.

3. Diethylcarbamazine resinate tablet 0% stearic acid

These tablets are prepared in accordance with Examples 1 and 3 above. Diethylcarbamazine resinate (16.4 g 3.28% W/W) is blended with minus 16 mesh desiccated liver (135 g 27.0%), microcrystalline cellulose (150.0 g 30.0% W/W) and minus 30 mesh Brewer's yeast (198.6 g 39.72% W/W). The blended materials are then formed into ¾-inch round tablets using the commercial tableting machine referred to above. The tablets weigh 2.27 g and contain no stearic acid.

4. Diethylcarbamazine resinate tablet containing 7% stearic acid

These tablets are prepared in the same manner as described above excepting that they contain diethylcarbamazine resinate 3.06% W/W, microcrystalline cellulose 30.0% W/W, desiccated liver 20.0% W/W, silicon dioxide 0.05% W/W, Brewer's yeast 39.89% W/W and stearic acid 7.0% W/W.

Test Formulations Compared for Palatability in Phase I, Phase II and Phase III Evaluations

A. Phase I

1. Conventional, non-resinated diethylcarbamazine tablets.
3. Edible tablet: Diethylcarbamazine resinate—0% stearic acid.
   Diethylcarbamazine resinate: 3.28%
   Microcrystalline cellulose: 30.0%
   Liver, desiccated granular: 27.0%
   Brewer's yeast: 39.72%

B. Phase II

2. Diethylcarbamazine resinate—binder
   Diethylcarbamazine resinate: 3.28%
   Microcrystalline cellulose: 96.72%
3. Edible tablet: Diethylcarbamazine resinate—0% stearic acid.
   Diethylcarbamazine resinate: 3.28%
   Microcrystalline cellulose: 30.0%
   Liver, desiccated granular: 27.0%
   Brewer's yeast: 39.72%

C. Phase III

4. Edible tablet: Diethylcarbamazine resinate—7% stearic acid
   Diethylcarbamazine resinate: 3.06%
   Microcrystalline cellulose: 30.0%
   Liver, desiccated granular: 20.0%
   Brewer's yeast: 39.89%
   Silicon dioxide: 0.05%

Stearic acid: 7.0%
5. Edible Tablet: Diethylcarbamazine resinate—0% stearic acid
Diethylcarbamazine resinate: 3.28%
Microcrystalline cellulose: 30.0%
Liver, desiccated granular: 27.0%
Brewer's yeast: 39.72%

The edible tablet listed as formulations 3 and 4 in Phase I, II and III, evaluations are compositions of the present invention. The total number of presentations of each formulation in each phase is 36 (nine dogs of four presentations per dog). The acceptance calculations are as follows:

| Phase/Formulation: | | No. Presentations | No. Acceptances | % Accepted |
|---|---|---|---|---|
| Phase I: | 1. Conventional Tablet | 36 | 0 | 0 |
| | 3. Edible Tablet (0% Stearic Acid) | 36 | 23 | 64 |
| Phase II: | 2. Tablet of Resinate and Binder | 36 | 1 | 3 |
| | 3. Edible Tablet (0% Stearic Acid) | 36 | 25 | 69 |
| Phase III: | 4. Edible Tablet (7% Stearic Acid) | 36 | 29 | 80 |
| | 3. Edible Tablet (0% Stearic Acid) | 36 | 29 | 80 |

Conclusions:
A. The edible tablet is far superior to a conventional tablet (reference Phase I).
B. The edible tablet matrix is essential over and above the use of a resinate for good acceptance, as the resinate/binder only tablet was poorly accepted (reference Phase II).
C. There is no effect on palatability (acceptance) related to the concentration of stearic acid between 0 and 7% of the total tablet weight (reference Phase III results).

EXAMPLE 5

Palatability evaluation of styrylpyridinium diethylcarbamazine edible tablets

The following tests are conducted to determine comparative acceptability of smaller tablets which provide the same dosage of 1-methyl-2-(p-chlorostyryl)-pyridinium resinate and diethylcarbamazine resinate and the larger tablets, both of which are contained within the essential "resinate", "liver", "yeast", matrix.

Nineteen clinically healthy dogs free from heartworm infection are used in this experiment. These animals are English Pointers, maintained at the University of Illinois Kennel and are used primarily in acceptability trials. The animals are, therefore, conditioned to accept or reject presented material based on palatability.

Two edible tablet formulations containing the same quantities of 1-methyl-2-(p-chlorostyryl)-pyridinium resinate and diethylcarbamazine resinate. Formulation A is a larger tablet (2.20 g) and Formulation B is a smaller tablet (0.70 g). The compositions of the tablets is summarized in Table I.

In Phase I, dogs in Group I are presented 1 edible tablet from the batch labeled "Formulation A" in the morning and 1 in the afternoon for 5 days. Likewise, dogs in Group II are presented 1 tablet from the batch labeled "Formulation B" in the morning and one in the afternoon for 5 days. Acceptance is noted as elapsed time before the tablet is consumed. If the tablet is not readily consumed, it is left with the dog for a period of 10 minutes and if not consumed by that time, is recorded as a rejection.

At the completion of Phase I, a crossover design is employed to minimize individual animal variation and Phase 2 is started. The dogs received tablets from the 2 formulation batches as described above following the same procedures as described in Phase I.

Acceptance and time to consumption is recorded.

The results of these tests are summarized in Table II, Table III and Table IV. Examination of the data contained in these tables shows the smaller tablet B to be equally palatable, being accepted 121 times with a mean time of consumption of 31 seconds when compared to larger tablet A which is accepted 132 times with a mean time of consumption of 39 seconds.

TABLE I

| Compositions of Tablets used in the evaluation | | |
|---|---|---|
| | Tablet A (2.2 g) | Tablet B (0.70 g) |
| Diethylcarbamazine (DEC) Resinate (Potency Av. = 45%) | 3.148 | 9.89 |
| Styrylpyridinium Resinate (Potency Av. = 48%) | 4.829 | 15.19 |
| Silicon Dioxide Colloidal NF | 0.050 | 0.05 |
| Liver, Desiccated, Granular | 20.000 | 20.00 |
| Brewers yeast | 34.973 | 17.87 |
| Cellulose, Microcrystalline NF | 30.000 | 30.00 |
| Stearic Acid USP | 7.000 | 7.00 |
| | 100.000 | 100.00 |

TABLE II

| Acceptability of the Test Tablets A and B | | | | | | | | | | | | | | | | | | | | |
|---|---|---|---|---|---|---|---|---|---|---|---|---|---|---|---|---|---|---|---|---|
| Formulation A | | | | | | | | | | | Formulation B | | | | | | | | | |
| Animal No. | Day 1 AM | PM | Day 2 AM | PM | Day 3 AM | PM | Day 4 AM | PM | Day 5 AM | PM | Animal No. | Day 1 AM | PM | Day 2 AM | PM | Day 3 AM | PM | Day 4 AM | PM | Day 5 AM | PM |
| Phase 1 | | | | | | | | | | | | | | | | | | | | | |
| 1 | | X | | | X | X | | | | X | 11 | | | | | | | | | | |
| 2 | X | X | | | | X | | X | X | | 12 | X | X | X | X | X | X | X | X | X | X |
| 3 | X | X | X | X | X | X | X | X | X | X | 13 | X | X | X | X | X | | X | | X | |
| 4 | X | X | X | X | | | X | X | X | X | 14 | X | X | X | X | | X | | X | X | X |
| 5 | X | X | | | | X | | | | | 15 | X | X | X | X | X | X | X | X | X | X |
| 6 | X | X | X | X | X | X | X | X | X | X | 16 | X | X | X | X | X | X | X | X | X | X |
| 7 | X | X | X | X | X | X | X | X | X | X | 17 | X | X | X | X | X | X | X | X | X | X |
| 8 | X | X | X | X | X | X | X | X | X | X | 18 | | | | | | | | | | |
| 9 | X | X | X | X | X | X | X | X | X | X | 19 | X | X | X | X | X | X | X | X | X | X |
| 10 | | | | | | | | | | | | | | | | | | | | | |
| Phase 2 | | | | | | | | | | | | | | | | | | | | | |
| 11 | | | | | | | | | | | 1 | | | | | | | | | | |
| 12 | X | X | X | X | X | X | X | X | X | X | 2 | X | X | X | X | X | X | X | X | X | X |
| 13 | X | X | | | | | | | | | 3 | X | X | X | X | X | X | X | X | X | X |
| 14 | X | X | X | X | X | X | | X | X | X | 4 | X | X | | X | X | | X | | | X |
| 15 | X | X | X | X | X | X | X | X | X | X | 5 | | | | | | | | | | |
| 16 | X | X | X | X | X | X | X | X | X | X | 6 | | | | | | | | | | |

TABLE II-continued

Acceptability of the Test Tablets A and B

| | Formulation A | | | | | | | | | | Formulation B | | | | | | | | | |
|---|---|---|---|---|---|---|---|---|---|---|---|---|---|---|---|---|---|---|---|---|
| Animal No. | Day 1 AM | PM | Day 2 AM | PM | Day 3 AM | PM | Day 4 AM | PM | Day 5 AM | PM | Animal No. | Day 1 AM | PM | Day 2 AM | PM | Day 3 AM | PM | Day 4 AM | PM | Day 5 AM | PM |
| 17 | X | X | X | X | X | X | X |   | X | X | 7 | X | X | X | X | X | X | X | X | X | X |
| 18 |   |   |   |   |   |   |   |   |   |   | 8 | X | X | X | X | X | X | X | X | X | X |
| 19 | X | X | X | X | X | X | X | X | X | X | 9 | X | X | X | X | X | X | X | X | X | X |
|   |   |   |   |   |   |   |   |   |   |   | 10 |   |   |   |   |   |   |   |   |   |   |

Total Accepted: Phase 1 = 72
Phase 2 = 60
132

Total Accepted: Phase 1 = 65
Phase 2 = 56
121

X = Indicates tablet accepted

TABLE III

Consumption Time of Formulation A

| | Day 1 | | Day 2 | | Day 3 | | Day 4 | | Day 5 | |
|---|---|---|---|---|---|---|---|---|---|---|
| | Animal | Time | Animal | Time | Animal | Time | Animal | Time | Animal | Time |
| PHASE 1 | 1 | 1:10 | 3 | 0:10 | 1 | 2:15 | 1 | 4:20 | 1 | 2:30 |
| | 2 | 4:45 | 3 | 0:05 | 1 | 0:35 | 2 | 3:10 | 2 | 2:20 |
| | 2 | 1:12 | 4 | 0:50 | 2 | 2:10 | 3 | 0:12 | 3 | 0:06 |
| | 3 | 0:02 | 4 | 0:22 | 3 | 0:16 | 3 | 0:08 | 3 | 0:05 |
| | 3 | 0:15 | 6 | 0:02 | 3 | 0:07 | 4 | 0:32 | 4 | 0:35 |
| | 4 | 2:05 | 6 | 0:05 | 4 | 0:35 | 4 | 0:30 | 4 | 0:25 |
| | 4 | 0:25 | 7 | 0:12 | 5 | 0:08 | 6 | 0:06 | 6 | 0:02 |
| | 5 | 1:15 | 7 | 0:02 | 6 | 0:12 | 6 | 0:09 | 6 | 0:02 |
| | 5 | 0:30 | 8 | 0:02 | 6 | 0:08 | 7 | 0:02 | 7 | 0:07 |
| | 6 | 0:02 | 8 | 0:07 | 7 | 0:05 | 7 | 0:04 | 7 | 0:08 |
| | 6 | 0:10 | 9 | 0:10 | 7 | 0:05 | 8 | 0:05 | 8 | 0:12 |
| | 7 | 0:20 | 9 | 0:02 | 8 | 0:06 | 8 | 0:09 | 8 | 0:06 |
| | 7 | 0:45 | 12 | 0:12 | 8 | 0:05 | 9 | 0:07 | 9 | 0:02 |
| | 8 | 0:10 | 12 | 0:08 | 9 | 0:06 | 9 | 0:06 | 9 | 0:02 |
| | 8 | 0:02 | 14 | 2:15 | 9 | 0:02 | 12 | 0:16 | 12 | 0:18 |
| | 9 | 0:15 | 14 | 1:45 | 12 | 0:10 | 12 | 0:12 | 12 | 0:45 |
| | 9 | 0:02 | 15 | 0:06 | 12 | 0:22 | 14 | 3:15 | 14 | 2:50 |
| PHASE 2 | 12 | 0:33 | 15 | 0:09 | 14 | 2:45 | 15 | 0:12 | 14 | 2:20 |
| | 12 | 0:12 | 16 | 0:15 | 14 | 3:40 | 16 | 0:11 | 15 | 0:18 |
| | 13 | 0:45 | 16 | 0:11 | 15 | 0:06 | 16 | 0:09 | 15 | 0:12 |
| | 13 | 1:35 | 17 | 0:19 | 15 | 0:08 | 16 | 0:05 | 16 | 0:04 |
| | 14 | 3:10 | 17 | 0:35 | 16 | 0:07 | 17 | 1:25 | 16 | 0:03 |
| | 14 | 4:05 | 19 | 0:21 | 16 | 0:15 | 19 | 0:10 | 16 | 0:50 |
| | 15 | 0:14 | 19 | 0:08 | 17 | 0:30 | 19 | 0:32 | 17 | 1:20 |
| | 15 | 0:18 | Total | 8:33 | 17 | 1:10 | Total | 16:07 | 19 | 0:45 |
| | 16 | 0:12 | | | 19 | 0:05 | | | 19 | 0:09 |
| | 16 | 0:10 | | | 19 | 0:18 | | | Total | 16:36 |
| | 17 | 1:40 | | | Total | 16:31 | | | | |
| | 17 | 0:55 | | | | | | | | |
| | 19 | 0:42 | | | | | | | | |
| | 19 | 0:30 | | | | | | | | |
| | Total | 28:26 | | | | | | | | |

Total Consumption Time = 86:13
Total Acceptances = 132
Mean Time of Consumption = 0:39

Note:
All times expressed as minutes:seconds
Animal numbers that repeat in the same day indicate AM and PM acceptance.

TABLE IV

Consumption Time of Formulation B

| | Day 1 | | Day 2 | | Day 3 | | Day 4 | | Day 5 | |
|---|---|---|---|---|---|---|---|---|---|---|
| | Animal | Time | Animal | Time | Animal | Time | Animal | Time | Animal | Time |
| PHASE 1 | 12 | 0:45 | 12 | 0:12 | 12 | 0:05 | 12 | 1:00 | 12 | 0:06 |
| | 12 | 0:10 | 12 | 0:05 | 12 | 0:45 | 12 | 0:07 | 12 | 0:35 |
| | 13 | 0:15 | 13 | 0:10 | 13 | 1:30 | 13 | 1:10 | 13 | 1:25 |
| | 13 | 2:05 | 13 | 0:22 | 14 | 0:10 | 14 | 1:25 | 14 | 1:10 |
| | 14 | 1:30 | 14 | 4:00 | 15 | 0:25 | 15 | 0:05 | 14 | 1:20 |
| | 14 | 0:45 | 14 | 1:05 | 15 | 0:08 | 15 | 0:04 | 15 | 0:06 |
| | 15 | 0:55 | 15 | 0:02 | 16 | 0:20 | 16 | 0:20 | 15 | 0:05 |
| | 15 | 0:02 | 15 | 0:14 | 16 | 0:02 | 16 | 0:02 | 16 | 0:02 |
| | 16 | 0:02 | 16 | 0:02 | 17 | 0:15 | 17 | 0:04 | 16 | 0:02 |
| | 16 | 0:05 | 16 | 0:06 | 17 | 0:12 | 17 | 0:05 | 17 | 0:05 |
| | 17 | 0:30 | 17 | 0:20 | 19 | 0:05 | 19 | 0:04 | 17 | 0:15 |

TABLE IV-continued

| | Consumption Time of Formulation B | | | | | | | | |
|---|---|---|---|---|---|---|---|---|---|
| | Day 1 | | Day 2 | | Day 3 | | Day 4 | | Day 5 | |
| | Animal | Time | Animal | Time | Animal | Time | Animal | Time | Animal | Time |
| | 17 | 0:10 | 17 | 0:06 | 19 | 0:05 | 19 | 0:07 | 19 | 0:06 |
| | 19 | 0:20 | 19 | 0:05 | 2 | 0:22 | 2 | 0:08 | 19 | 0:08 |
| | 19 | 0:02 | 19 | 0:04 | 2 | 0:06 | 2 | 0:14 | 2 | 0:20 |
| PHASE 2 | 2 | 0:20 | 2 | 0:11 | 3 | 1:15 | 3 | 2:40 | 2 | 0:21 |
| | 2 | 0:12 | 2 | 0:15 | 3 | 3:30 | 3 | 0:45 | 3 | 1:10 |
| | 3 | 3:50 | 3 | 1:05 | 4 | 0:30 | 4 | 1:20 | 3 | 2:35 |
| | 3 | 2:15 | 3 | 1:35 | 7 | 0:03 | 7 | 0:05 | 4 | 4:15 |
| | 4 | 0:33 | 4 | 0:45 | 7 | 0:06 | 7 | 0:07 | 7 | 0:07 |
| | 4 | 0:50 | 7 | 0:05 | 8 | 0:07 | 8 | 0:08 | 7 | 0:04 |
| | 7 | 0:03 | 7 | 0:04 | 8 | 0:08 | 8 | 0:12 | 8 | 0:09 |
| | 7 | 0:06 | 8 | 0:04 | 9 | 0:05 | 9 | 0:03 | 8 | 0:15 |
| | 8 | 0:05 | 8 | 0:04 | 9 | 0:05 | 9 | 0:04 | 9 | 0:10 |
| | 8 | 0:10 | 9 | 0:07 | Total | 10:19 | Total | 10:19 | 9 | 0:08 |
| | 9 | 0:08 | 9 | 0:06 | | | | | Total | 14:59 |
| | 9 | 0:12 | Total | 11:14 | | | | | | |
| | Total | 16:20 | | | | | | | | |

Total Consumption Time = 63:11
Total Acceptances = 121
Mean Time of Consumption = 0:31

Note:
All times expressed as minutes:seconds
Animal numbers that repeat in the same day indicate AM and PM acceptance.

EXAMPLE 6

Palatability evaluation of styrylpyridinium diethylcarbamazine edible tablets

The following tests are conducted to determine comparative acceptability of smaller tablets which provide the same dosage of diethylcarbamazine resinate and the larger tablets, both of which are contained within the essential "resinate", "liver", "yeast", matrix.

Twenty clinically healthy dogs free from heartworm infection are used in this experiment. These animals are English Pointers, maintained at the University of Illinois Kennel and are used primarily in acceptability trials. The animals are, therefore, conditioned to accept or reject presented material based on palatability.

Two edible tablet formulations containing the same quantities of diethylcarbamazine resinate. Formulation A is a larger tablet (6.60 g) and Formulation B is a smaller tablet (2.1 g). The compositions of the tablets is summarized in Table V.

In Phase I, dogs in Group I are presented 1 edible tablet from the batch labeled "Formulation A" in the morning and 1 in the afternoon for 5 days. Likewise, dogs in Group II are presented 1 tablet from the batch labeled "Formulation B" in the morning and one in the afternoon for 5 days. Acceptance is noted as elapsed time before the tablet is consumed. If the tablet is not readily consumed, it is left with the dog for a period of 10 minutes and if not consumed by that time, is recorded as a rejection.

At the completion of Phase I, a crossover design is employed to minimize individual animal variation and Phase 2 is started. The dogs received tablets from the 2 formulation batches as described above following the same procedures as described in Phase I.

Acceptance and time to consumption is recorded.

The results of these tests are summarized in Table VI, Table VII and Table VIII. Examination of the data contained in these tables shows the smaller tablet B to be equally palatable, being accepted 103 times with a mean time of consumption of 72 seconds when compared to larger tablet A which is accepted 104 times with a mean time of consumption of 73 seconds.

TABLE V

| Compositions of Tablets used in the evaluation | | |
|---|---|---|
| | Tablet A (6.6 g) | Tablet B (2.1 g) |
| Diethylcarbamazine (DEC) Resinate (Potency Av. = 49.4%) | 2.95 | 10.289 |
| Silicon Dioxide Colloidal NF | 0.05 | 0.05 |
| Brewers yeast | 40.0 | 32.652 |
| Cellulose, Microcrystalline NF | 30.0 | 30.0 |
| Stearic Acid USP | 7.0 | 7.0 |
| Liver, Desiccated, Granular | 20.0 | 20.0 |
| | 100.00 | 100.000 |

TABLE VI

| Acceptability of the test tablets | | | | | | | | | | | | | | | | | | | | |
|---|---|---|---|---|---|---|---|---|---|---|---|---|---|---|---|---|---|---|---|---|
| | Formulation A | | | | | | | | | | Formulation B | | | | | | | | | |
| Animal No. | Day 1 | | Day 2 | | Day 3 | | Day 4 | | Day 5 | | Animal No. | Day 1 | | Day 2 | | Day 3 | | Day 4 | | Day 5 | |
| | AM | PM | AM | PM | AM | PM | AM | PM | AM | PM | | AM | PM | AM | PM | AM | PM | AM | PM | AM | PM |
| | | | | | | | | | | | Phase 1 | | | | | | | | | | |
| 1 | | | | | X | | X | | | | 11 | X | X | X | | | X | | | X | X |
| 2 | | | | X | | | | | | | 12 | | | | X | | X | X | | X | X |
| 3 | | X | | | | | X | | | | 13 | X | X | X | X | | | X | X | | |
| 4 | X | | | | X | | | | X | X | 14 | X | X | X | X | X | | | X | | X |
| 5 | | | X | | | X | | | X | X | 15 | X | | | | X | X | | | | |
| 6 | X | | X | X | X | | X | | X | | 16 | | | | X | X | | | | X | X |
| 7 | X | X | X | X | X | X | X | X | | | 17 | X | X | | | | | | | X | |
| 8 | X | | X | X | | | X | X | X | X | 18 | X | | | X | | | X | X | X | X |

TABLE VI-continued

Acceptability of the test tablets

| | Formulation A | | | | | | | | | | Formulation B | | | | | | | | | | |
|---|---|---|---|---|---|---|---|---|---|---|---|---|---|---|---|---|---|---|---|---|---|
| Animal No. | Day 1 | | Day 2 | | Day 3 | | Day 4 | | Day 5 | | Animal No. | Day 1 | | Day 2 | | Day 3 | | Day 4 | | Day 5 | |
| | AM | PM | AM | PM | AM | PM | AM | PM | AM | PM | | AM | PM | AM | PM | AM | PM | AM | PM | AM | PM |
| 9 | | | | | | X | X | X | X | X | 19 | X | X | X | X | X | | X | X | | X |
| 10 | X | | | X | | X | | X | | | 20 | X | X | X | X | X | | | X | X | |
| | | | | | | | | | | | Phase 2 | | | | | | | | | | |
| 11 | X | X | X | X | | | X | X | X | | 1 | X | X | | | X | X | | X | X | X |
| 12 | | | | | | | | | | | 2 | | | | | | | | | | |
| 13 | X | X | X | | | | X | | X | X | 3 | X | X | | | X | X | X | X | X | X |
| 14 | | | | X | X | X | X | X | X | X | 4 | | | | X | | | | X | | X |
| 15 | | | X | | | | X | X | X | X | 5 | | | X | | | X | | X | | |
| 16 | | X | | | | X | | | | | 6 | X | | X | | | | X | X | | |
| 17 | X | | X | X | | | X | X | X | | 7 | X | X | X | | | X | X | X | | |
| 18 | X | | X | X | X | X | X | | X | X | 8 | | | X | X | X | | X | X | X | X |
| 19 | | X | X | X | X | | X | X | | X | 9 | | | X | | | | | | X | |
| 20 | X | X | X | X | X | X | X | X | X | X | 10 | | | | X | | X | X | X | X | X |

Total Accepted: Phase 1 = 45
Phase 2 = 59
104

Total Accepted: Phase 1 = 56
Phase 2 = 47
103

X = Indicates tablet accepted

TABLE VII

Consumption Time of Formulation - A

| | Day 1 | | Day 2 | | Day 3 | | Day 4 | | Day 5 | |
|---|---|---|---|---|---|---|---|---|---|---|
| | Animal | Time | Animal | Time | Animal | Time | Animal | Time | Animal | Time |
| PHASE 1 | 4 | 4:15 | 3 | 1:30 | 1 | 3:10 | 1 | 1:30 | 1 | 0:25 |
| | 6 | 0:25 | 5 | 0:45 | 2 | 8:00 | 3 | 0:20 | 4 | 0:10 |
| | 7 | 0:30 | 6 | 1:10 | 4 | 0:45 | 5 | 0:10 | 5 | 3:15 |
| | 7 | 0:15 | 6 | 0:30 | 5 | 2:10 | 5 | 2:30 | 5 | 0:50 |
| | 8 | 0:20 | 7 | 8:00 | 6 | 3:15 | 6 | 0:35 | 6 | 0:45 |
| | 10 | 2:30 | 7 | 2:00 | 7 | 0:50 | 7 | 1:00 | 8 | 1:10 |
| | 11 | 0:20 | 8 | 3:00 | 7 | 1:00 | 7 | 0:20 | 8 | 0:30 |
| | 11 | 0:10 | 8 | 0:15 | 9 | 3:30 | 8 | 0:15 | 9 | 0:40 |
| | 13 | 1:15 | 10 | 3:30 | 10 | 1:10 | 8 | 0:45 | 9 | 0:15 |
| | 13 | 0:20 | 11 | 2:10 | 14 | 0:05 | 9 | 0:50 | 11 | 0:30 |
| | 16 | 1:00 | 11 | 1:30 | 14 | 0:10 | 9 | 3:20 | 11 | 1:00 |
| | 17 | 3:15 | 13 | 0:40 | 16 | 1:15 | 10 | 6:00 | 13 | 0:10 |
| PHASE 2 | 18 | 0:25 | 14 | 0:05 | 18 | 4:30 | 11 | 0:30 | 13 | 0:45 |
| | 19 | 2:15 | 15 | 0:10 | 18 | 0:40 | 11 | 1:20 | 14 | 1:45 |
| | 20 | 0:30 | 17 | 0:10 | 19 | 0:15 | 13 | 0:10 | 14 | 0:30 |
| | 20 | 0:10 | 17 | 0:45 | 20 | 0:15 | 14 | 0:10 | 15 | 0:45 |
| | Total | 17:55 | 18 | 1:00 | 20 | 0:25 | 14 | 0:15 | 15 | 2:30 |
| | | | 18 | 0:55 | Total | 31:25 | 15 | 1:15 | 17 | 0:20 |
| | | | 19 | 0:30 | | | 15 | 0:50 | 18 | 0:30 |
| | | | 19 | 0:30 | | | 17 | 0:50 | 18 | 0:45 |
| | | | 20 | 0:20 | | | 17 | 0:30 | 19 | 0:10 |
| | | | 20 | 0:10 | | | 18 | 0:50 | 20 | 2:30 |
| | | | Total | 29:35 | | | 19 | 0:05 | 20 | 0:55 |
| | | | | | | | 19 | 3:10 | Total | 21:05 |
| | | | | | | | 20 | 0:10 | | |
| | | | | | | | 20 | 0:10 | | |
| | | | | | | | Total | 27:05 | | |

Total Consumption Time = 127:05
Total Acceptances = 104
Mean Time of Consumption = 1:13

Note:
All times expressed as minutes:seconds
Animal numbers that repeat in the same day indicate AM and PM acceptance.

TABLE VIII

Consumption Time of Formulation - B

| | Day 1 | | Day 2 | | Day 3 | | Day 4 | | Day 5 | |
|---|---|---|---|---|---|---|---|---|---|---|
| | Animal | Time | Animal | Time | Animal | Time | Animal | Time | Animal | Time |
| PHASE 1 | 11 | 1:10 | 11 | 6:00 | 11 | 0:45 | 12 | 9:00 | 11 | 0:35 |
| | 13 | 0:20 | 11 | 0:35 | 12 | 1:10 | 13 | 0:40 | 11 | 0:10 |
| | 14 | 4:00 | 12 | 0:15 | 13 | 0:45 | 14 | 0:30 | 12 | 0:20 |
| | 14 | 0:45 | 13 | 0:20 | 14 | 0:25 | 16 | 1:15 | 12 | 1:00 |
| | 15 | 1:10 | 13 | 0:35 | 15 | 1:30 | 18 | 2:40 | 13 | 4:00 |
| | 17 | 0:30 | 14 | 0:40 | 15 | 0:40 | 18 | 0:10 | 14 | 8:30 |
| | 18 | 0:10 | 14 | 0:20 | 16 | 0:20 | 19 | 1:40 | 16 | 0:40 |
| | 19 | 0:25 | 16 | 2:15 | 18 | 0:20 | 19 | 0:05 | 17 | 0:20 |

TABLE VIII-continued

| | Consumption Time of Formulation - B | | | | | | | | |
|---|---|---|---|---|---|---|---|---|---|
| | Day 1 | | Day 2 | | Day 3 | | Day 4 | | Day 5 | |
| | Animal | Time | Animal | Time | Animal | Time | Animal | Time | Animal | Time |
| | 19 | 0:55 | 17 | 0:10 | 19 | 0:15 | 20 | 1:20 | 18 | 0:15 |
| | 20 | 0:30 | 18 | 0:25 | 20 | 0:25 | 1 | 1:10 | 18 | 0:15 |
| | 20 | 1:10 | 19 | 0:10 | 1 | 0:14 | 1 | 3:00 | 19 | 0:20 |
| | 1 | 0:40 | 19 | 0:40 | 3 | 0:20 | 3 | 2:30 | 20 | 1:15 |
| | 1 | 0:10 | 20 | 0:15 | 3 | 0:10 | 3 | 0:40 | 1 | 8:00 |
| | 3 | 1:00 | 20 | 0:45 | 5 | 0:20 | 4 | 5:00 | 1 | 3:00 |
| PHASE 2 | 3 | 0:45 | 1 | 1:50 | 7 | 0:10 | 5 | 1:45 | 3 | 3:45 |
| | 5 | 2:30 | 4 | 0:20 | 8 | 1:10 | 6 | 0:30 | 3 | 0:40 |
| | 6 | 0:50 | 6 | 0:35 | 10 | 0:05 | 6 | 0:10 | 4 | 1:10 |
| | 7 | 1:30 | 7 | 0:15 | Total | 9:35 | 7 | 0:40 | 7 | 0:50 |
| | 7 | 0:30 | 8 | 1:45 | | | 7 | 0:30 | 8 | 0:10 |
| | Total | 18:00 | 8 | 0:35 | | | 8 | 0:10 | 8 | 0:10 |
| | | | 9 | 0:45 | | | 8 | 0:05 | 9 | 1:30 |
| | | | Total | 19:30 | | | 10 | 0:45 | 10 | 4:00 |
| | | | | | | | 10 | 0:50 | 10 | 0:30 |
| | | | | | | | Total | 35:05 | Total | 41:25 |

Total Consumption Time = 123:35
Total Acceptances = 103
Mean Time of Consumption = 1:12

Note:
All times expressed as minutes:seconds
Animal numbers that repeat in the same day indicate AM and PM acceptance.

What is claimed is:

1. A palatable anthelmintic resinate composition comprising from greater than 5% to about 11% by weight of a resinated N,N-dialkylpiperazine carboxamide compound having the structural formula:

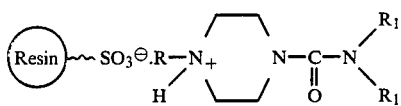

wherein R is hydrogen or alkyl $C_1$-$C_6$ and $R_1$ is alkyl $C_1$-$C_5$ and wherein the resin is a high capacity sulfonic cationic exchange resin of the polystyrene-divinylbenzene type having a particle size of less than 800μ; from greater than 7% to 16% by weight of a resinated styrylpyridinium compound having the structural formula:

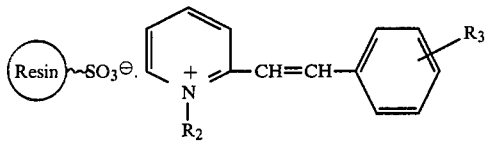

wherein $R_2$ is alkyl $C_1$-$C_4$, $R_3$ is hydrogen or halogen and the resin is a high capacity sulfonic cationic exchange resin of the polystyrene-divinylbenzene type having a particle size of less than 800μ; 18% to 60% by weight of dessiccated liver; 0 to 40% by weight of Brewer's yeast; 23.95% to 31% by weight of microcrystalline cellulose, 0% to 7% by weight of stearic acid; and 0% to 0.05% by weight of sodium aluminum silicate or silicon dioxide.

2. The composition according to claim 1 wherein the resin has an average particle size range between 45 and 300μ.

3. A method for controlling helminthiasis in companion animals comprising administering to said animals one to four, 0.70 gram chewable tablets daily, said tablets containing, as the essential ingredients, from greater than 5% to about 11% by weight of resinated diethylcarbamazine wherein the resin is a high capacity sulfonic cationic exchange resin of the polystyrenedivinylbenzene type; from greater than 7% to 16% by weight of a resinated compound having the structural formula:

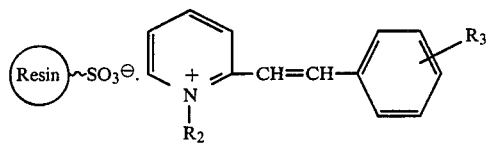

wherein $R_2$ is alkyl $C_1$-$C_4$, $R_3$ is hydrogen or halogen and the resin is a high capacity sulfonic cationic exchange resin of the polystyrene-divinylbenzeye type; 18% to 60% by weight of desiccated liver; from 0% to 40% by weight of Brewer's yeast; 23.95% to 31% by weight of microcrystalline cellulose; 0% to 7% by weight of stearic acid and 0% to 0.05% by weight of sodium aluminum silicate or silicon dioxide.

4. A palatable anthelmintic resinate composition comprising from greater than 5% to about 11% by weight of a resinated N,N-dialkylpiperazine carboxamide compound having the structural formula:

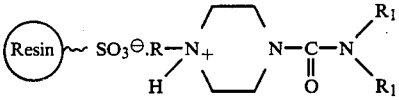

where R is hydrogen or alkyl $C_1$-$C_6$ and $R_1$ is alkyl $C_1$-$C_5$ and wherein the resin is a high capacity sulfonic cationic exchange resin of the polystyrene-divinylbenzene type having a particle size of less than 800μ; 18% to 60% by weight of dessicated liver; 0% to 40% by weight of Brewer's yeast; 23.95% to 31% by weight of microcrystalline cellulose, 0% to 7% by weight of stearic acid; and 0% to 0.05% by weight of sodium aluminum silicate or silicon dioxide.

5. The composition according to claim 4 wherein the resin has an average particle size range between 45 and 300μ.

6. A method for controlling helminthiasis in companion animals comprising administering to said animals one to four 2.1 gram chewable tablets daily, said tablets containing, as the essential ingredients, from greater than 5% to about 11% by weight of resinated diethylcarbamazine wherein the resin is a high capacity sulfonic cationic exchange resin of the polystyrene-divinylbenzene type; 18% to 60% by weight of dessicated liver; from 0% to 40% by weight of Brewer's yeast; 23.95% to 31% by weight of microcrystalline cellulose; 0% to 7% by weight of stearic acid and 0% to 0.05% by weight of sodium aluminum silicate or silicon dioxide.

7. A palatable anthelmintic resinate composition comprising from 0% to 16% by weight of a resinated styrylpyridinium compound having the structural formula:

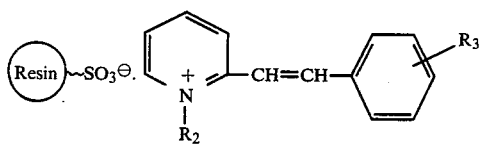

wherein $R_2$ is alkyl $C_1$-$C_4$, $R_3$ is hydrogen or halogen and the resin is a high capacity sulfonic cationic exchange resin of the polystyrene-divinylbenzene type having a particle size of less than 800μ; 18% to 60% by weight of dessicated liver; 0% to 40% by weight of Brewer's yeast; 23.95% to 31% by weight of microcrystalline cellulose, 0% to 7% by weight of stearic acid; and 0% to 0.05% by weight of sodium aluminum silicate or silicon dioxide.

8. The composition according to claim 7 wherein the resin has an average particle size range between 45 and 300μ.

9. A method for controlling helminthiasis in companion animals comprising administering to said animals one to four, 2.1 gram chewable tablets daily, said tablets containing, as the essential ingredients, from 0% to 16% by weight of a resinated compound having the structural formula:

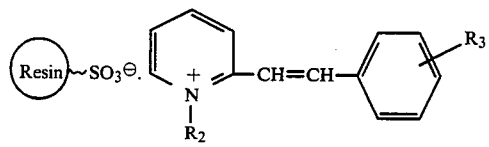

wherein $R_2$ is alkyl $C_1$-$C_4$, $R_3$ is hydrogen or halogen and the resin is a high capacity sulfonic cationic exchange resin of the polystyrene-divinylbenzene type; 18% to 60% by weight of dessiccated liver; from 0% to 40% by weight of Brewer's yeast; 23.95% to 31% by weight of microcrystalline cellulose; 0% to 7% by weight of stearic acid and 0% to 0.05% by weight of sodium aluminum silicate or silicon dioxide.

* * * * *